United States Patent [19]

Mori et al.

[11] 3,972,432

[45] Aug. 3, 1976

[54] METHOD FOR ROTATIONALLY POSITIONING A WELDED STEEL PIPE IN RESPONSE TO A SEAM SECTION THEREOF AND AN APPARATUS FOR POSITIONING THE SAME

[75] Inventors: Toshihiro Mori, Yokohama; Katsujiro Watanabe, Tokyo; Akihiko Nishisaka, Yokohama, all of Japan

[73] Assignee: Nippon Kokan Kabushiki Kaisha, Tokyo, Japan

[22] Filed: Feb. 19, 1975

[21] Appl. No.: 550,958

[30] Foreign Application Priority Data

Feb. 21, 1974 Japan............................. 49-20750

[52] U.S. Cl.............................. 214/340; 214/152
[51] Int. Cl.².............................................. B65G 7/00
[58] Field of Search................... 214/1 Q, 340, 152

[56] References Cited
UNITED STATES PATENTS

R28,413    5/1975    Evans et al. ................. 214/340

*Primary Examiner*—Robert G. Sheridan
*Attorney, Agent, or Firm*—Flynn & Frishauf

[57] ABSTRACT

Disclosed is an apparatus for rotationally positioning a welded steel pipe in response to a seam section thereof which comprises a driving means for subjecting the welded steel pipe to a high speed-normal rotation and low speed-counter rotation about its axis, a detecting signal-generating means including an AC bridge circuit, a sensor disposed close to the surface of the welded steel pipe, a differential amplifier and a synchronous detector, to produce, when the welded steel pipe makes a high speed-normal rotation, a negative peak voltage signal and in succession a positive peak voltage signal in response to the seam section of the welded steel pipe and to produce, when the welded steel pipe makes a low speed-back rotation. a positive peak voltage signal and in succession a negative peak voltage signal in response to said seam section, a first Schmitt circuit for producing an output when the level of said detecting signal has exceeded the zero level, a second Schmitt circuit for producing an output when the level of said detecting signal has exceeded a positive specified level, a flip-flop circuit set in response to the rising operation of the second Schmitt circuit output and reset in response to the falling operation of the first Schmitt circuit output, a monostable multivibrator for producing an output pulse signal having a prescribed time width in response to the falling operation of the flip-flop circuit output, and means for controlling said driving means for said welded steel pipe so that when the monostable multivibrator has produced an output pulse signal during said high speed-normal rotation, the welded steel pipe is changed-over from the high speed-normal rotation to the low speed-back rotation; and when the monostable multivibrator has produced an output pulse signal during said low speed-counter rotation, the welded steel pipe is promptly stopped.

7 Claims, 8 Drawing Figures

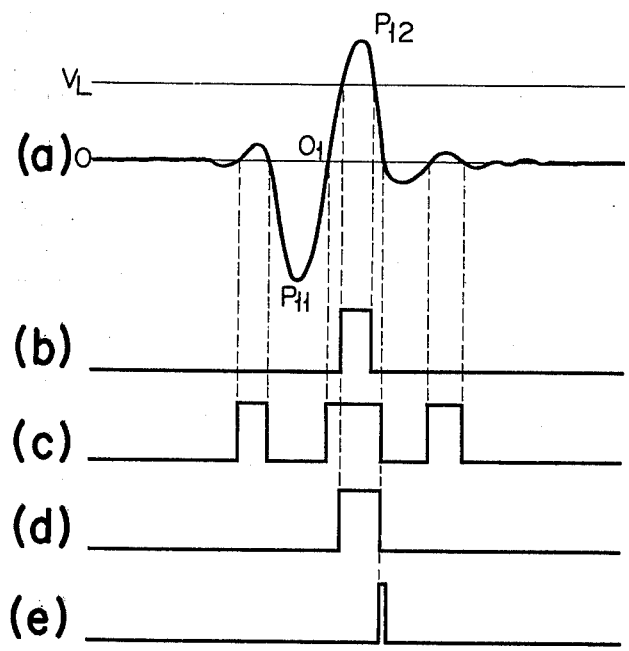
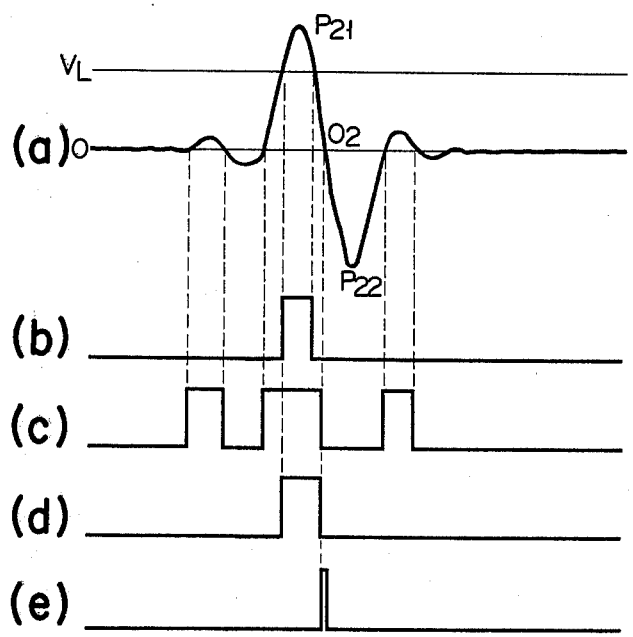

HIGH SPEED CONTROL CIRCUIT  TIMER CIRCUIT  LOW SPEED CONTROL CIRCUIT

METHOD FOR ROTATIONALLY POSITIONING A WELDED STEEL PIPE IN RESPONSE TO A SEAM SECTION THEREOF AND AN APPARATUS FOR POSITIONING THE SAME

This invention relates to a method and apparatus for rotationally positioning a welded steel pipe, and more particularly to a method and apparatus for rotationally positioning the welded steel pipe in response to a seam section thereof in order to locate the seam section at a position wherein the seam section is opposed to, for example, a seam section examining means.

Generally, it is necessary to position as desired the seam section of the welded steel pipe, in order to perform the pipe welding in case of before welding and in order to examine the welded portion in case of after welding.

Conventionally, as the method for setting the seam section of such welded steel pipe to a desired position there is known a method which comprises disposing a mechanical seam detector for detecting the seam section of the welded steel pipe so as to be in contact with the surface of the welded steel pipe, subjecting the welded steel pipe to a low speed rotation through the operation of a rotation driving mechanism and yet controlling the rotation driving mechanism in response to the output from said seam detector, and stopping the rotation of the welded steel pipe when the seam detector has detected the seam section of the welded steel pipe, thereby to set the seam section of the welded steel pipe to the desired position. In this case, as said mechanical seam detector there is used, for example, a mechanical limit switch, which, when, in case of after welding, the detecting rod of the limit switch has slided up on the convex welded portion of the seam section and when, in case of before welding, said detecting rod has fallen into the opening portion of the seam section, is operated to detect the seam section of the welded steel pipe.

However, the foregoing conventional method has the drawbacks that since the seam section is mechanically detected, it can not be detected with high precision; and the apparatus makes an erroneous operation due to the vibration or distortion of the welded steel pipe or due to the variation in the convex welded portion or opening portion of the seam section, failing to precisely position the seam section as desired. Further, the conventional method has the drawbacks that since the welded steel pipe is all along subjected to a low speed rotation for being positioned, the positioning operation can not quickly be carried out; and where, conversely, the welded steel pipe is subjected to a high speed rotation, the pipe rotation is stopped at a position in which the seam section is much overrun beyond a desired position due to the pipe rotation inertia, failing to position the seam section with precision although the positioning operation is performed speedily.

Accordingly, it is the object of the invention to provide a method and apparatus for rotationally positioning a welded steel pipe in response to a seam section thereof which is capable of quickly and precisely positioning the seam section as desired.

SUMMARY OF THE INVENTION

According to one aspect of this invention there is provided a method for rotationally positioning a welded steel pipe in response to a seam section thereof comprising disposing two electromagnetic sensitive impedance elements in a manner approaching said welded steel pipe and spaced from each other circumferentially of said welded steel pipe so as to permit the distance between said two impedance elements to be rendered substantially equal to the width of said seam section of said welded steel pipe, rotating said welded steel pipe to obtain in response to said two impedance elements a detecting signal having a reference potential at its center portion and those peak potentials at portions preceding and succeeding said center portion which are positive or negative with respect to said reference potential, and stopping the rotation of said welded steel pipe when said detecting signal exceeds a specified level previously set in a direction positive or negative with respect to said reference potential and returns to said reference potential.

According to another aspect of this invention there is provided a method for rotationally positioning a welded steel pipe in response to a seam section thereof utilizing both high speed-normal rotation and low speed-counter rotation. The method comprises disposing two electromagnetic sensitive impedance elements in a manner approaching said welded steel pipe and spaced from each other circumferentially of said welded steel pipe so as to permit the distance between said two impedance elements to be rendered substantially equal to the width of said seam section of said welded steel pipe, subjecting said welded steel pipe to a high speed-normal rotation to obtain a detecting signal having a first peak voltage of one polarity and in succession a second peak voltage of the opposite polarity in response to the impedance variation of said two impedance elements occurring in response to said seam section, stopping the high speed-normal rotation of said welded steel pipe when said second peak voltage has exceeded a specified level and then subjecting said welded steel pipe to a low speed-counter rotation, and stopping said low speed-counter rotation of said welded steel pipe when said second peak voltage has once again exceeded said specified level during said low speed-counter rotation.

According to further aspect of this invention there is provided an apparatus for rotationally positioning a welded steel pipe in response to a seam section thereof comprising a driving means including a motor, for subjecting said welded steel pipe to a high speed-normal rotation and low speed-counter rotation about its axis, a sensor including first and second electromagnetic sensitive impedance elements juxtaposed in a manner approaching the outer surface of said welded steel pipe and spaced at a prescribed distance from each other circumferentially of said welded steel pipe, means for obtaining a detecting signal having a first peak voltage of one polarity and in succession a second peak voltage of the opposite polarity with the zero level interposed between said first and second peak voltages, in response to the impedance variation occurring in said first and second impedance elements in response to said seam section, a signal treating circuit for obtaining a pulse signal having a prescribed pulse width in response to said second peak voltage, and a control circuit for said driving means intended to change-over the rotation of said welded steel pipe from said high speed-normal rotation to said low speed-counter rotation when a pulse output has been produced from said signal treating circuit during said high speed-normal rotation and to stop said low speed-counter rotation of said welded steel pipe when a pulse output has been once again produced from said signal treating circuit during said low speed-counter rotation.

BRIEF DESCRIPTION OF THE DRAWINGS

This invention can be more fully understood from the following detailed description when taken in conjunction with the accompanying drawings, in which:

FIGS. 4 and 5 illustrate output signal waveforms for explaining the operation of the apparatus illustrated in FIG. 1;

DETAILED DESCRIPTION

Figure 1:
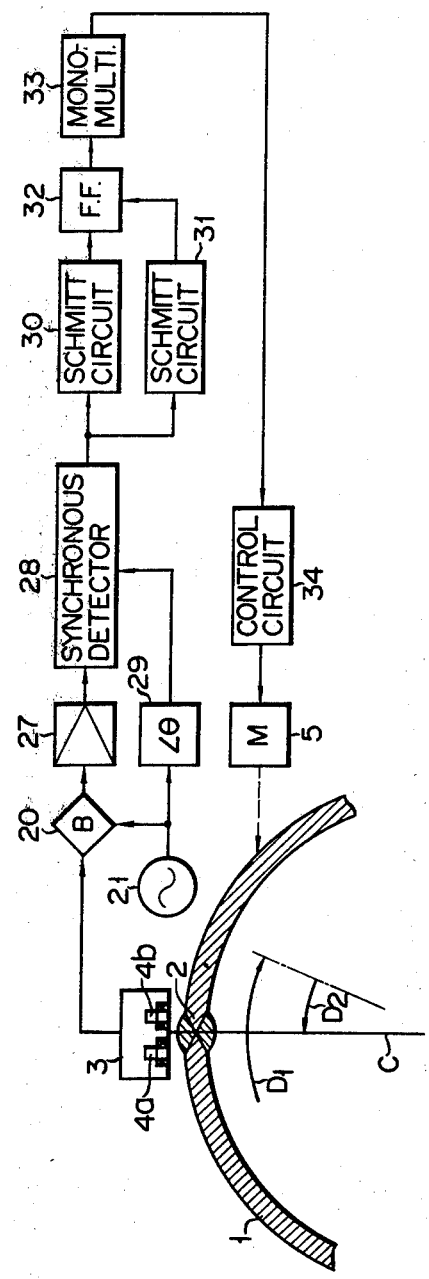
FIG. 1 is a block circuit diagram illustrating an apparatus for rotationally positioning a welded steel pipe in response to a seam section thereof according to an embodiment of the invention.

Referring to FIG. 1, a welded steel pipe 1 is set on turning rollers as later described so as to be rotated about its axis in a direction indicated by an arrow D1 or D2. A reference numeral 2 designates a seam section of the welded steel pipe. A sensor 3 having two detecting coils 4a, 4b is provided close to the outer surface of the welded steel pipe 1. The detecting coils 4a, 4b are disposed within the sensor 3 so that the respective center axes of the coils are located on opposite sides of a straight line C connecting the center axis of the pipe 1 to the center of the seam section 2 so as to permit the distance between the center axes of the coils to be rendered substantially equal to the width of the seam section 2. The respective detecting coils 4a, 4b are constructed, for example, such that a winding is wound a hundred times about a ferrite core 10 mm in diameter and 20 mm in length, and the sensor 3 is constructed such that such coils are molded in a resin with their center axis-to-center axis interval set at 25 mm.

Figure 2:
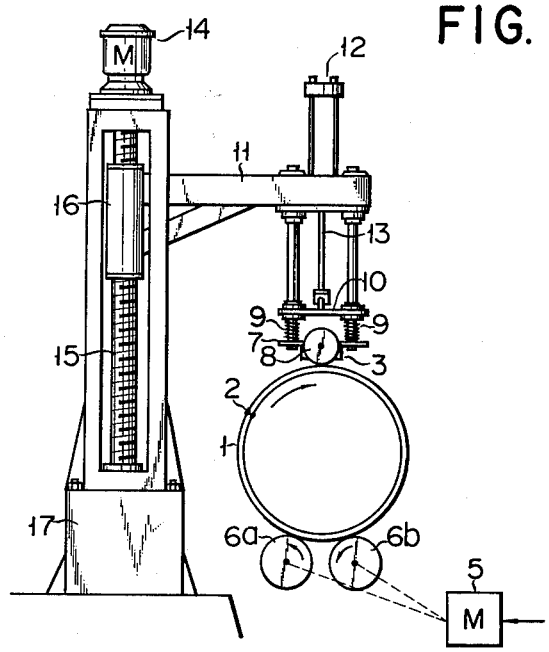
FIG. 2 is a schematic view illustrating a supporting mechanism for the sensor of FIG. 1 and the construction of a rotation-driving means for the welded steel pipe.

The welded steel pipe 1 is rotated in a state set on the turning rollers 6a, 6b being driven by a motor 5 as illustrated in FIG. 2. The sensor 3 is mounted on a support plate 7 jointly with a guide roller 8. The distance between the lower end of the sensor 3 and the outer surface of the pipe 1 is always kept constant, for example, 10 mm, by means of a guide roller 8. The support plate 7 is connected through support or buffer springs 9 to a suspending member 10. Even if, therefore, the pipe 1 has, for example, an irregular or distorted surface portion, the guide roller 8 will be securely kept in contact with the outer surface of the pipe 1. The suspending member 10 is connected to the operating rod 13 of an air cylinder 12 mounted on an arm 11, and the guide roller 8 is always pressed under a specified pressure against the outer surface of the pipe 1 by the air cylinder 12. The stroke of the operating rod 13 of the air cylinder 12 is set, for example, at 300 mm. The arm 11 is fixed at one end to a support member 16 in engagement with a raising and lowering screw shaft 15 rotated by a manually controllable raising and lowering motor 14, and arrangement is so made that the height of the arm 11 can be varied with the outer diameter of the pipe 1 through driving the motor 14. The screw shaft 15 is connected at the upper end to the motor 14 and rotatably supported at the lower end on a support bed 17.

Figure 3:
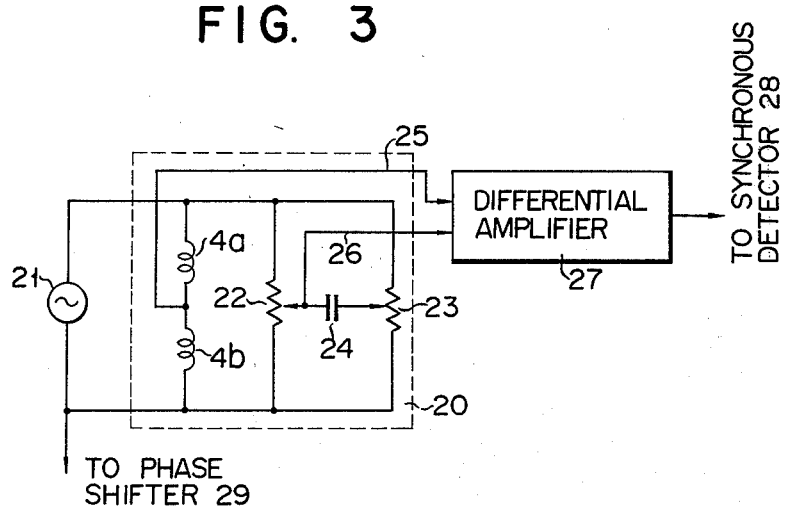
FIG. 3 is a circuit diagram illustrating a concrete example of the bridge circuit illustrated in FIG. 1.

The detecting coils 4a, 4b are connected in series between the output terminals of an AC reference signal generator 21 so as to constitute two arms of an AC bridge circuit 20, as illustrated in FIG. 3. Between the output terminals of the AC reference signal generator 21 are connected in parallel the variable resistors 22, 23 of the AC bridge circuit 20. A capacitor 24 is connected between the respective sliding terminals of the variable resistors 22, 23. For example, the variable resistors 22, 23 are respectively set to 1 kL while the capacitor 24 is set to 500 pF. The output of the AC bridge circuit 20 is coupled to the input terminals of a differential amplifier 27 through lines 25, 26, starting with the connection point between the detecting coils 4a, 4b and the connection point between the sliding terminal of the variable resistor 22 and the capacitor 24, respectively.

Turning back to FIG. 1, the output of the differential amplifier 27 is supplied to the input terminal of a synchronous detector 28. To the reference signal input terminal of the synchronous detector 28 is supplied the output from the reference signal generator 21 as a reference phase signal through a phase shifter 29. The output frequency of the reference signal generator 21 is set, for example, at 50 kHz. The AC bridge circuit 20 is for the purpose of obtaining an output signal whose voltage and phase vary with the impedance variation in the coils 4a, 4b occurring, when the seam section 2 passes by the coils 4a, 4b, due to the electric and magnetic nature difference between the welded portion and the pipe body portion of the seam section 2. Further, the phase shifter 29 is so set that the output phase of the reference signal generator 21 is shifted by an angle at which the output of the synchronous detector 28 produced due to the passage by the sensor 3 of the seam section 2 has a maximum level.

In the synchronous detector 28, the output signal of the AC bridge circuit 20 is subjected to phase analysis utilizing the output of the phase shifter 29 as the reference phase signal. For example, the phase shifting amount of the phase shifter 29 is so set beforehand that when the center of the seam section 2 has been brought into coincidence with the center line equidistantly spaced from the coils 4a, 4b as illustrated in FIG. 1, the output level of the synchronous detector 28 is rendered zero. Namely, the phase shifting amount of the phase shifter 29 and the mutual connection of coils 4a, 4b are so set beforehand that the output voltage levels of the coils 4a, 4b are rendered mutually opposite in polarity with respect to the line 25 of FIG. 3. For example, the mutual connection relationship between the coils 4a, 4b is so set that when the pipe 1 has made a normal rotation, a negative output is obtained from the coil 4a and yet a positive output is obtained from the coil 4b. Conversely, this connection relationship may of course be so set that in case of the normal rotation a positive output is obtained from the coil 4b. The output of the synchronous detector 28 set as such is as illustrated in FIG. 4(a), wherein P11 is a negative peak output obtained from the coil 4a in case of the normal rotation; P12 is a positive peak output obtained from the coil 4b in the same case; and O1 is an output level when the center of the seam section 2 has been brought into coincidence with the center line between the coils 4a, 4b.

In FIG. 1, the output of the synchronous detector 28 is supplied to two Schmitt circuits 30, 31. The Schmitt circuit 30 is so set as to produce such an output as illustrated in FIG. 4(b) when the output level of the synchronous detector 28 has exceeded a level of VL, while the Schmitt circuit 31 is so set as to produce such an output as illustrated in FIG. 4(c) when the output level of the synchronous detector 28 has exceeded a level of 0 volt. The output of the Schmitt circuit 30 is input to the set terminal of a flip-flop circuit 32, which is set when the output of the Schmitt circuit 30 has risen. The output of the Schmitt circuit 31 is input to the reset terminal of the flip-flop circuit 32, which is reset when the output of the Schmitt circuit 31 has fallen. Thus, the output from the flip-flop circuit 32, in case of the pipe 1 making a high speed-normal rotation, is obtained in response to the peak output P12 as illustrated in FIG. 4(d). The output of the flip-flop circuit 32 is fed to a monostable multivibrator 33, from which is obtained that output pulse illustrated in FIG. 4(e) which rises in response to the fall of the output from the flip-flop circuit 32 and yet has a relatively narrow pulse width. Note here that in this invention it is necessary, for the purpose of preventing the apparatus from making an erroneous operation due to the noise signals, that the setting level VL for the Schmitt circuit 30 is so set as to have a polarity opposite to that of the peak output P11 initially obtained during the high speed-normal rotation.

The output of the monostable multivibrator 33 is supplied to a control circuit 34 for controlling the motor 5. When, in case of the pipe 1 making a high speed-normal rotation, the output from the monostable multivibrator 33 is delivered to the control circuit 34, the control circuit 34 first produces an output signal for stopping the rotation of the motor 5 and then produces a command signal for the low speed-counter rotation of the pipe 1 in a prescribed length of time after the stopping signal has been produced. Namely, even if the motor 5 is stopped upon receipt of the stopping signal, the pipe 1 will continue to be rotated for a while due to the rotation inertia of the pipe 1. In consideration of this rotation time, therefore, a specified length of time is set between when producing the stopping signal and when producing the command signal.

When the pipe 1 is caused to make a counter rotation in a direction indicated by the arrow D2 of FIG. 1, the seam section detecting output from the synchronous detector 28 is as illustrated in FIG. 5(a). Namely, there is obtained from the Schmitt circuit 30 such an output as in FIG. 5(b) in response to a detecting output of more than the level VL in the peak output P21, while there is obtained from the Schmitt circuit 31 such an output as in FIG. 5(c) in response to a detecting output of more than 0 level. Accordingly, the respective outputs from the flip-flop circuit 32 and the monostable multivibrator 33 are as illustrated in FIGS. 5(d) and 5(e). In this manner, the output from the monostable multivibrator 33, in case of the low speed-counter rotation of the pipe 1, is obtained when the center of the sensor 3 has coincided with the center of the seam section 2. When the output from the monostable multivibrator 33 is applied to the control circuit 34, a motor stoppage-commanding signal is supplied from the control circuit 34 to the motor 5, causing the motor 5, accordingly the pipe 1, to be stopped. In this case, the pipe 1 is required to be rotated at a speed low enough to permit the pipe 1 to be at once stopped when the motor 5 has been stopped. Thus, the pipe 1 is stopped at a position in which the center of the sensor 3 coincides with the center of the seam section 2.

Figure 7:
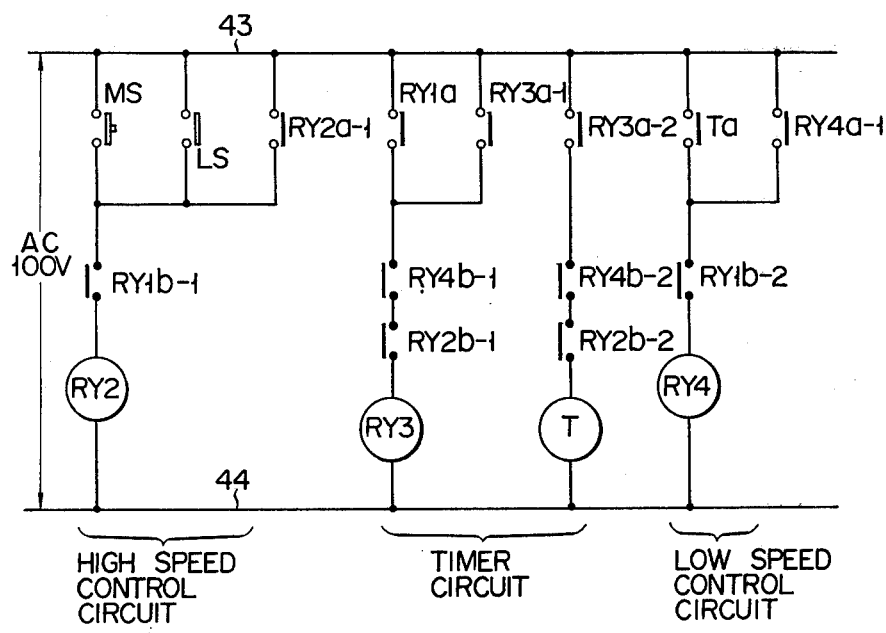
FIGS. 6 and 7 are circuit diagrams each illustrating a concrete example of the rotation controlling circuit illustrated in FIG. 1.
Figure 6:
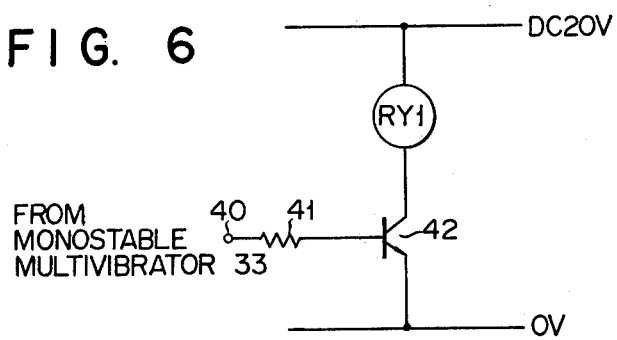

There will now be described the construction of the control circuit 34 by reference to FIGS. 6, 7 and 8. In FIG. 6, the output from the monostable multivibrator 33 of FIG. 1 is applied to an input terminal 40, which is connected through a resistor 41 to the base of a transistor 42. The collector of the transistor 42 is connected through a relay RY1 to a source line having a DC voltage of 20 volt, while the emitter thereof is connected directly to a ground line having a voltage of 0 volt. That is, arrangement is so made that when a positive input is applied to the input terminal 40, the transistor 42 is rendered conductive to energize the relay RY1. One end of a first normally closed contact pair RY1 b-1 of the relay RY1 is connected to one end of a relay RY2 included in the control circuit of FIG. 7, while one end of a second normally closed contact pair RY1 b-2 thereof is connected to one end of a relay RY4. To the other end of the normally closed contact pair RY1 b-1 are connected at one end a manually operable switch MS, a limit switch LS and a first normally opened contact pair RY 2a-1 of the relay RY2, which are connected at the other end to one line 43 of an AC source having a voltage of, for example, 100 volt, the other line 44 of the AC source being connected to the other end of the relay RY2. The limit switch LS is provided in association with the turning rollers 6a, 6b and is so designed as to be turned-on when the pipe 1 has been placed on the turning rollers 6a, 6b. It is to be noted here that the limit switch LS can be provided also in association with an operating circuit for the air cylinder 12, though it is not illustrated; and when the limit switch LS is turned-on, the air cylinder 12 is lowered to permit the sensor 3 to be brought to a desired position of the outer wall of the pipe 1. Further, the manual switch MS is manually closed by an operator checking that the pipe 1 has been placed on the turning rollers 6a, 6 b. The circuit associated with the relay RY2 is a control circuit for permitting the motor 5 to make a high speed-normal rotation.

Between the source lines 43 and 44 having the AC voltage of 100 volt are further connected in series a normally opened contact pair RY1a, respective normally closed contact pairs RY 4b-1 and RY 2b-1 of the relays RY4 and RY2, and a relay RY3. To the normally opened contact pair RY1a is connected in parallel a first normally opened contact pair RY 3a-1 of the relay RY3. Between the source lines 43 and 44 are further connected in series a second normally opened RY 3pair RY3a-2 of the relay RY3, respective normally closed contact pairs RY 4b-2 and RY 2b-2 of the relays RY4 and RY2, and a time-delay relay T. A circuit including the relay RY3 and the time-delay T is a timer circuit, which is used to temporarily stop the motor 5 for a specified length of time when the motor 5 is changed-over from the high speed-normal rotation to the low speed-counter rotation.

Between the source lines 43 and 44 are further connected in series a normally opened contact pair Ta of the time-delay relay T, a normally closed contact pair RY 1b-2 of the relay RY1, and a relay RY4. To the normally opened contact pair Ta is connected in parallel a normally opened contact pair RY 4a-1 of the relay RY4. The circuit associated with the relay RY4 is a control circuit for permitting the motor 5 to make a low speed-counter rotation.

Figure 8:
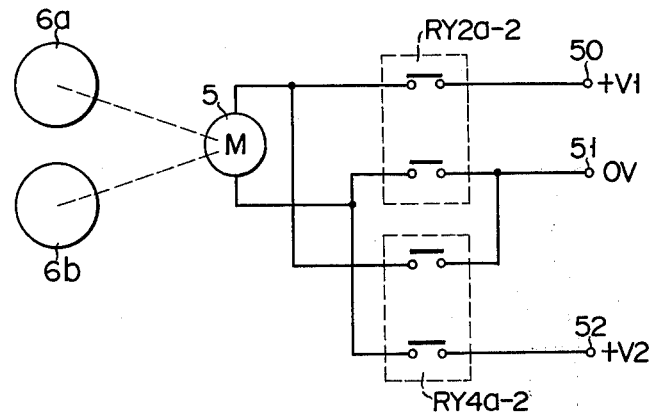
FIG. 8 illustrates a driving circuit for driving the motor of FIG. 1 in association with the rotation control circuit illustrated in FIGS. 6 and 7.

In FIG. 8, the motor 5 is connected between DC source terminals 50 and 51 through two normally opened contact pairs RY 2a-2 and also is connected between the DC source terminal 51 and a DC source terminal 52 through two normally opened contact pairs RY 4a-2. A relatively high positive voltage (of +V1 volt) is applied across the source terminals 50, 51, while a positive voltage (of + V2 volt) lower than the + V1 volt across the source terminals 51 and 52. When the normally opened contact pairs RY 2a-2 are closed, the motor 5 is subjected to a high speed-normal rotation. When the normally opened contact pairs RY 4a-2 are closed, the motor 5 is subjected to a low speed-counter rotation.

There will now be described the present method for rotationally positioning the welded steel pipe 1 in response to the seam section thereof, using the apparatus having the foregoing construction. First, when the pipe 1 as welded is placed on the turning rollers 6a, 6b, the limit switch LS is turned-on. This causes the air cylinder 12 to be driven, and as a result the sensor 3 is downwardly moved approximately 30 cm. Next, the raising and lowering motor 14 is driven to downwardly move the arm 11, and when the guide roller 8 has been brought into contact with the output surface of the pipe 1, the arm 11 is stopped. Since, in this case, the desired position at which the seam section 2 is to be stopped is located right on the uppermost portion of the pipe 1, the sensor 3 is situated right above the pipe 1. But the sensor 3 may of course be provided, for example, downwardly of the pipe 1 correspondingly to said desired position. Under the condition wherein the guide roller 8 is in contact with the pipe 1 in the above-mentioned manner, the vertical vibration of the pipe 1 will be absorbed by the buffer springs 9 if in the range of approximately ± 25 mm.

When the operator checks said condition and turns-on the manual switch MS, the relay RY2 is energized to close the first and second normally opened contact pairs RY 2a-1 and RY 2a-2 and simultaneously to open the normally closed contact pairs RY 2b-1 and RY 2b-2. As a result, the relay RY2 is self-maintained by its normally opened contact pair RY 2a-1, and simultaneously the motor 5 is supplied with a high voltage of + V1. This causes the motor 5 to make a high speed-normal rotation, which causes the pipe 1 to make a high speed-normal rotation through the turning rollers 6a, 6b in a direction indicated by the arrow D1 of FIG. 1 at a peripheral speed of, for example, 18 m/mm. Since, in this state, the contact pairs RY 2b-1, RY 2b-2 and Ta are opened, the timer circuit and the low speed control circuit remain inoperative.

When the seam section 2 is brought just in front of the sensor 3 during the high speed-normal rotation of the pipe 1, a detecting signal is obtained from the AC bridge circuit 20 in response to the impedance variation of the detecting coils 4a, 4b due to the electric and magnetic variation of the seam section 2. This detecting signal, after amplified by the differential amplifier 27, is fed to the synchronous detector 28, from which is obtained such a detecting signal as illustrated in FIG. 4(a). As previously mentioned, this detecting signal is sent to a signal treating circuit comprising the Schmitt circuits 30, 31, flip-flop circuit 32, and monostable multivibrator 33. From the monostable multivibrator 33 is obtained that pulse signal illustrated in FIG. 4(e) which has a pulse width of, for example, 0.5 sec. This pulse signal is delivered to the input terminal 40 of FIG. 6 included in the motor control circuit 34. Upon receipt of this pulse signal, the transistor 42 is rendered conductive to energize the relay RY1. As a result, the normally closed contact pair RY 1b-1 is opened to deenergize the relay RY2. Thus, the motor 5 is stopped. Even when the motor 5 is stopped, the pipe 1 heretofore subjected to the high speed-normal rotation is further rotated for, for example, approximately 2 seconds due to the rotation inertia and stopped. Actually, therefore, the pipe rotation is stopped at a position in which the seam section 2 is a little advanced in the arrow D1-indicated direction from the sensor position.

When the relay RY1 is energized and the relay RY2 is deenergized, the relay contact pairs RY1a and RY 2b-1 are closed to energize the relay RY3. As a result, the normally opened contact pair RY 3a-1 is closed to cause the relay RY3 to be self-maintained and simultaneously to cause the contact pairs RY 3a-2 and RY 2b-2 to be closed to energize the time-delay relay T. Thus, the timer circuit commences to operate. This time-delay relay T is so set as to have a delay time of, for example, 2 seconds. Accordingly, the normally opened contact pair Ta of the relay T is closed in 2 seconds after the relay T is energized. Within said delay time of the relay T the pipe 1 rotated due to the inertia is stopped without the aid of any manual operation.

When the normally opened contact pair Ta of the relay T is closed, the relay RY4 is energized because, at this time, the contact pair of RY 1b-2 is already in a closed state. The energization of the relay RY4 causes the normally opened contact pair RY 4a-1 to be closed to cause the relay RY4 to be self-maintained, and simultaneously causes the normally opened contact pair RY 4a-2 to be closed to cause the motor 5 to be connected through the terminals 51, 52 to the low voltage source (+ V2). The motor 5 is supplied with a low voltage of + V2 to cause a current to flow in the opposite direction to that in case of the high speed-normal rotation, and therefore starts to make a low speed-counter rotation. As a result, the pipe 1 is caused to make a low speed-counter rotation through the turning rollers 6a, 6b in the opposite direction to that indicated by the arrow D1, namely, in the arrow D2-indicated direction. In this case, the circumferential speed of the pipe 1 is set at, for example, 1.8 m/min.

When the pipe 1 is counter-rotated to cause the seam section 2 to be again brought just in front of the sensor 3, there is obtained from the synchronous detector 28 such a detecting signal as is illustrated in FIG. 5(a). When, at this time, there appears the initial peak output P21, the pulse output as illustrated in FIG. 5(e) from the monostable multivibrator 33 of the signal treating circuit is applied to the input terminal 40 of the circuit in FIG. 6 to energize the relay RY1 once again. The pulse output shown in FIG. 5(e) is produced correspondingly to the point O2 of the waveform of FIG. 5(a), namely, at the time when the center of the sensor 3 has coincided with the center of the seam section 2. The above-mentioned energization of the relay RY1 causes the normally closed contact pair RY 1b-1 to be opened to deenergize the relay RY2. As a result, the normally closed contact pair RY 2b-2 is opened to deenergize the relay RY4. The deenergization of the relay RY4 causs the normally opened contact pair RY 4a-2 to be opened, so that the low speed-counter rotation of the motor 5 is stopped. In case of this low speed-counter rotation, the circumferential speed of the pipe 1 is as extremely low as, for example, 1.8 m/min. Accordingly, the rotation inertia of the pipe 1 itself is also extremely small. As a result, the pipe 1 is stopped simultaneously with the stoppage of the motor 5, and the seam section 2 is situated at a position in which it is placed just in front of the sensor 3.

In the preceding embodiment, the level VL for setting the operation of the Schmitt circuit 30 is set on the positive side so that, in case of the high speed-normal rotation, first the negative peak output P11 and then the positive peak output P12 can be obtained as illustrated in FIG. 4(a). But conversely, arrangement may be so made that, in case of the high speed-normal rotation, first the positive peak output P21 and then the negative peak output P22 can be obtained as illustrated in FIG. 5(a). In the latter case, the operation setting level VL for the Schmitt circuit 30 has only to be set at a negative value slightly higher than the negative peak output P22, so that when the input level of the Schmitt circuit 31 becomes negative, the Schmitt circuit 31 can produce an output. In any case, the operating setting level VL for the Schmitt circuit 30 should be so set that no erroneous operation occurs due to noise signals; and when, in case of the low speed-counter rotation in particular, the center of the sensor 3 has coincided with the center of the seam section 2, there is obtained a stoppage-commanding signal for the motor 5.

What we claim is:

1. A method for rotationally positioning a welded steel pipe in response to a seam section thereof comprising disposing two electromagnetic sensitive impedance elements in a manner approaching said welded steel pipe and spaced from each other circumferentially of said welded steel pipe so that the distance between said two impedance elements is substantially equal to the width of said seam section of said welded steel pipe, rotating said welded steel pipe to obtain a detecting signal which, when said both sensitive impedance elements have been brought into coincidence with said seam section of said welded pipe, becomes a reference potential the polarity of said detecting signal being thereafter inverted with respect to said reference potential, and stopping the rotation of said welded steel pipe when said detecting signal has exceeded a specified preset level and has returned to said reference potential.

2. A method for rotationally positioning a welded steel pipe in response to a seam section thereof comprising disposing two electromagnetic sensitive impedance elements in a manner approaching said welded steel pipe and spaced from each other circumferentially of said welded steel pipe so that the distance between said two impedance elements is substantially equal to the width of said seam section of said welded steel pipe, subjecting said welded steel pipe to a high speed-normal rotation to obtain a detecting signal having a first peak voltage of one polarity and in succession a second peak voltage of the opposite polarity in response to the impedance variation of said two impedance elements occurring in response to said seam section, stopping the high speed-normal rotation of said welded steel pipe when said second peak voltage has exceeded a specified level and then subjecting said welded steel pipe to a low speed-counter rotation, and stopping said low speed-counter rotation of said welded steel pipe when said second peak voltage has once again exceeded said specified level during said low speed-counter rotation.

3. An apparatus for rotationally positioning a welded steel pipe in response to a seam section thereof comprising a driving means including a motor, for subjecting said welded steel pipe to a high speed-normal rotation and low speed-counter rotation about its axis, a sensor including first and second electromagnetic sensitive impedance elements juxtaposed in a manner approaching the outer surface of said welded steel pipe and spaced at a prescribed distance from each other circumferentially of said welded steel pipe, means for obtaining a detecting signal having a first peak voltage of one polarity and in succession a second peak voltage of the opposite polarity with the zero level interposed between said first and second peak voltages, in response to an impedance variation occurring in said first and second impedance elements in response to said seam section, a signal treating circuit for obtaining a pulse signal having a prescribed pulse width in response to said second peak voltage, and a control circuit for said driving means to change-over the rotation of said welded steel pipe from said high speed-normal rotation to said low speed-counter rotation when a pulse output has been produced from said signal treating circuit during said high speed-normal rotation and to stop said low speed-counter rotation of said welded steel pipe when a pulse output has been once again produced from said signal treating circuit during said low speed-counter rotation.

4. An apparatus according to claim 3 wherein said driving means includes a plurality of turning rollers for receiving said welded steel pipe thereon, and a motor for rotating said plurality of turning rollers.

5. An apparatus according to claim 3 wherein said means for obtaining said detecting signal includes an AC bridge circuit having said first and second impedance elements in its arms, a differential amplifier for amplifying the output from said AC bridge circuit, a synchronous detector having an input terminal supplied with the output from said differential amplifier, and means including a phase shifter for supplying a reference phase signal to said synchronous detector.

6. An apparatus according to claim 3 wherein said signal treating circuit includes a first Schmitt circuit for producing an output when said detecting signal has a specified level between said second peak voltage and said zero level, a second Schmitt circuit for producing an output when said detecting signal has exceeded said zero level in the direction of the same polarity as that of said specified level, a flip-flop circuit set in response to a rising of the output from said first Schmitt circuit and reset in response to a falling of the output from said second Schmitt circuit, and a monostable multi-vibrator driven in response to falling of the setting output from said flip-flop circuit to produce a pulse signal having said prescribed pulse width.

7. An apparatus according to claim 3 wherein said control circuit for said driving means comprises a high speed control circuit including a first relay having contacts for connecting said motor to a high voltage source for said high speed-normal rotation of said welded steel pipe, an energization circuit for said first relay, a second relay having first normally closed contacts connected to said energization circuit and energized in response to said pulse signal sent from said signal treating circuit during said high speed-normal rotation, a timer circuit including a time-delay relay energized during the deenergization of said first relay and set so as to have a prescribed length of delay time, a low speed control circuit including a third relay energized when said time-delay relay of said timer circuit is operated and having contacts for connecting said motor to a low voltage source for said low speed-counter rotation of said welded steel pipe, and second normally closed contacts provided in association with said second relay and opened when said second relay is energized, to deenergize said third relay to thereby stop said motor.

* * * * *